United States Patent [19]

Chou et al.

[11] Patent Number: 4,525,587
[45] Date of Patent: Jun. 25, 1985

[54] PROCESS FOR PREPARING A CEPHALOSPORIN COMPOUND

[75] Inventors: Ta-Sen Chou; Perry C. Heath, both of Indianapolis, Ind.

[73] Assignee: Eli Lilly and Company, Indianapolis, Ind.

[21] Appl. No.: 576,609

[22] Filed: Feb. 3, 1984

Related U.S. Application Data

[63] Continuation-in-part of Ser. No. 453,445, Dec. 27, 1982, abandoned.

[51] Int. Cl.$^3$ .................. C07D 501/38; A61K 31/565
[52] U.S. Cl. .................................................. 544/025
[58] Field of Search ........................... 544/25; 424/246

[56] References Cited

U.S. PATENT DOCUMENTS 4,369,313  1/1983  Jones et al. ............................ 544/24
4,433,141  2/1984  Jones et al. ............................ 544/25

*Primary Examiner*—Nicholas S. Rizzo
*Attorney, Agent, or Firm*—Charles W. Ashbrook; Arthur R. Whale

[57] ABSTRACT

(6R,7R)-7-[(Z)-2-(2-triphenylmethylaminothiazol-4-yl)-2-(2-tert.-butoxycarbonylprop-2-oxyimino)acetamido]-3-(1-pyridiniummethyl)ceph-3-em-4-carboxylate is isolated by formation of N,N-dimethylacetamide solvates.

3 Claims, No Drawings

PROCESS FOR PREPARING A CEPHALOSPORIN COMPOUND

CROSS-REFERENCE TO RELATED APPLICATIONS

This is a continuation-in-part of Ser. No. 453,445 filed Dec. 27, 1982, now abandoned.

BACKGROUND OF THE INVENTION

U.S. Pat. No. 4,258,041 describes the synthesis of (6R, 7R)-7-[(Z)-2-(2-aminothiazol-4-yl)-2-(2-carboxyprop-2-oxyimino)acetamido]-3-(1-pyridiniummethyl)ceph-3-em-4-carboxylate, a cephalosporin antibiotic now generically known as ceftazidime. The reported synthesis of ceftazidime comprises reacting (Z)-2-(2-tert.-butoxycarbonylprop-2-oxyimino)-2-(2-triphenylmethylaminothiazol-4-yl)acetyl chloride with (6R,7R)-7-amino-3-(1-pyridiniummethyl)ceph-3-em-4-carboxylic acid in a mixture of N,N-dimethylacetamide and acetonitrile to provide the ceftazidime intermediate, (6R,7R)-7-[(Z)-2-(2-triphenylmethylaminothiazol-4-yl)-2-(2-tert.-butoxycarbonylprop-2-oxyimino)acetamido]-3-(1-pyridiniummethyl)ceph-3-em-4-carboxylate. This ceftazidime intermediate was recovered from the reaction mixture as an amorphous solid that was subsequently purified by crystallization of an N,N-dimethylformamide solvate (2½ moles of DMF per mole of intermediate) from N,N-dimethylformamide. The ceftazidime intermediate was then reacted with formic acid to effect removal of the protecting groups and to provide ceftazidime.

An object of the present invention is to provide an improved process for preparing the ceftazidime intermediate, whereby the intermediate is crystallized directly out of the reaction mixture as an N,N-dimethylacetamide solvate. The practice of this invention obviates the need for subsequent purification and thus provides improved yields and reduced costs in the production of ceftazidime.

SUMMARY OF THE INVENTION

This invention concerns an improvement in a process for the preparation of an intermediate that is useful in the production of ceftazidime. More particularly, this invention provides an improvement in a process for preparing (6R,7R)-7-[(Z)-2-(2-triphenylmethylaminothiazol-4-yl)-2-(2-tert.-butoxycarbonylprop-2-oxyimino)acetamido]-3-(1-pyridiniummethyl)ceph-3-em-4-carboxylate (ceftazidime intermediate) by reacting a ((Z)-2-(2-tert.-butoxycarbonylprop-2-oxyimino)-2-(2-triphenylmethylaminothiazol-4-yl)acetyl halide with (6R,7R)-7-amino-3-(1-pyridiniummethyl)ceph-3-em-4-carboxylic acid dihydrochloride, the improvement comprising carrying out the reaction in N,N-dimethylacetamide (DMAC) so as to form an N,N-dimethylacetamide solvate which can be isolated as a crystalline solid directly from the reaction mixture. The process of this invention permits the isolation in good yield of a substantially pure N,N-dimethylacetamide solvate of the ceftazidime intermediate. In a further embodiment of the invention there is provided a crystalline N,N-dimethylacetamide solvate of the formula

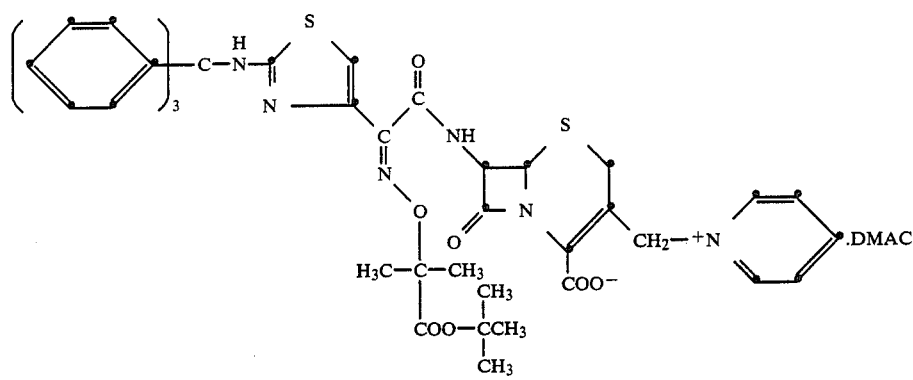

having substantially the following x-ray powder diffraction pattern:

| d | I/I$_1$ |
|---|---|
| 16.07 | 1.00 |
| 10.53 | .12 |
| 9.72 | .12 |
| 9.07 | .72 |
| 8.23 | .04 |
| 7.66 | .24 |
| 7.17 | .04 |
| 6.84 | .04 |
| 6.30 | .24 |
| 6.01 | .16 |
| 5.77 | .16 |
| 5.42 | .24 |
| 5.25 | .16 |
| 4.82 | .20 b |
| 4.51 | .44 |
| 4.25 | .24 |
| 4.10 | .36 |
| 3.84 | .20 |
| 3.69 | .08 |
| 3.61 | .08 |
| 3.47 | .04 |
| 3.35 | .04 | b = broad

DETAILED DESCRIPTION OF THE INVENTION

When used herein, "ceftazidime intermediate" means (6R, 7R)-7-[(Z)-2-(2-triphenylmethylaminothiazol-4-yl)-2-(2-tert.-butoxycarbonylprop-2-oxyimino)acetamido]-3-(1-pyridiniummethyl)ceph-3-em-4-carboxylate. The process by which ceftazidime intermediate is prepared involves a typical acylation reaction comprising reacting a caphalosporin nucleus (i.e. a 7-amino-3-cephem derivative) with an acid halide, typically an acid chloride. The acid halide typically employed in the synthesis of ceftazidime intermediate is a (Z)-2-(2-tert.-butoxycarbonylprop-2-oxyimino)-2-(2- triphenylmethylaminothiazol-4-yl)acetic acid halide. The acylation reaction generally is accomplished by reacting the acid halide with about an equimolar quantity of the 7-amino-3-cepham nucleus in an unreactive solvent such as dichloromethane, acetone, or a mixture of N,N-dimethylacetamide and acetonitrile, and in the presence of a base such as triethylamine or pyridine. The improvement in the acylation process provided by this invention comprises employing N,N-dimethylacetamide as the reaction solvent, so as to produce the ceftazidime intermediate directly from the acylation reaction mixture as a crystalline N,N-dimethylacetamide solvate. This improved process obviates the need for a separate purification step in which ceftazidime intermediate is converted to a solvate such as the N,N-dimethylformamide solvate.

In carrying out the process of this invention, the acid halide, for instance (Z)-2-(2-tert.-butoxycarbonylprop-2-oxyimino)-2-(2-triphenylmethylaminothiazol-4-yl)acetyl chloride, is generally prepared by reaction of the free acid with a halogenating agent such as phosphorus pentachloride in a suitable solvent such as dichloromethane or diethyl ether. Once the acid halide is formed, it normally is not isolated but rather is simply added to a suspension of about an equimolor quantity of the cephalosporin nucleus in N,N-dimethylacetamide. A suitable base such as triethylamine is normally added to the reaction mixture to serve as scavanger for any free acid that might be present. The acylation reaction typically is substantially complete within about fifteen to ninety minutes when carried out at a temperature of about −20° to about 40° C. The ceftazidime intermediate that is thus produced is an N,N-dimethylacetamide solvate having the formula counter solvent of choice is diethyl ether, or a combination of diethyl ether and ethyl acetate.

Once the counter solvent is added to the N,N-dimethylacetamide reaction mixture containing ceftazidime intermediate, the ceftazidime intermediate N,N-dimethylacetamide solvate generally starts precipitating out of solution within about thirty to about ninety minutes when the solution is stirred at about −10° to about +10° C. The crystalline solvate is readily isolated by simply filtering the mixture, and it generally is desirable to wash the solvate with fresh N,N-dimethylacetamide or diethyl ether or a mixture thereof. The product can be air dried at room temperature or dried in vacuum to remove any excess solvents. The product thus produced is a crystalline N,N-dimethylacetamide solvate of ceftazidime intermediate having a purity generally greater than about ninety percent.

The ceftazidime intermediate DMAC solvate provided by this invention can be employed directly in the production of ceftazidime. For example, the crystalline solvate can be dissolved in an acid solution such as 98% formic acid to effect cleavage of the triphenylmethyl protecting group on the amino group attached to the thiazolylacetamido side chain, and the product can be added to hydrochloric acid to effect cleavage of the tert.-butoxy protecting group on the oxime portion of the side chain, and to form the dihydrochloride salt of ceftazidime, thereby facilitating isolation as a crystalline precipitate. The ceftazidime dihydrochloride can be employed as an antibiotic.

The following detailed examples illustrate the process improvement provided by this invention.

EXAMPLE 1

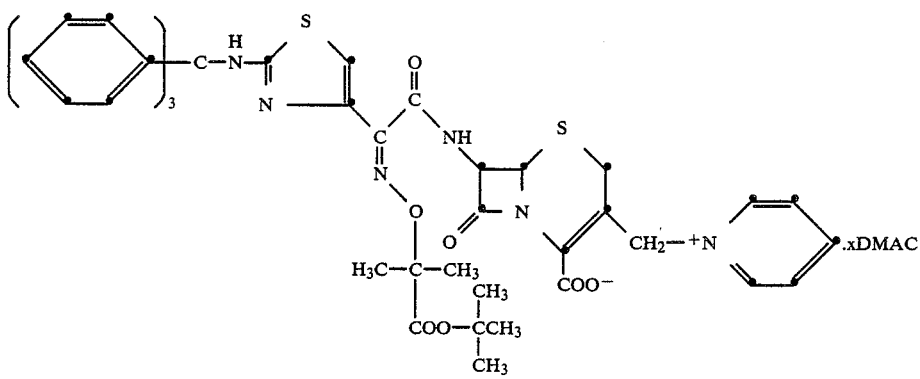

wherein DMAC is N,N-dimethylacetamide and x is a number from 0.5 to 3.0 and denotes the moles of DMAC per mole of ceftazidime intermediate. Preferred solvates are those wherein x is about 0.5 to about 1.5, and especially wherein X is about 1.0 and said crystal form has essentially the x-ray powder diffraction pattern listed above when measured with a 114.6 mm Debye-Scherrer camera using a nickel-filtered copper target tube.

The ceftazidime intermediate solvate provided by this invention can be readily isolated if desired by washing the reaction mixture with water and then adding a suitable counter solvent, i.e. a solvent in which ceftazidime intermediate is substantially insoluble. Typical counter solvents include ethers such as diethyl ether, methyl ethyl ether, diglyme, tetrahydofuran; and esters such as ethyl acetate, methyl acetate, and the like. The (6R,7R)-7-[(Z)-2-(2-triphenylmethylaminothiazol-4-yl)-2-(2-tert.-butoxycarbonylprop-2-oxyimino)acetamido]-3-(1-pyridiniummethyl)ceph-3-em-4-carboxylate.

To a cold (−10° C.) stirred solution of 8.70 g (41.8 mm) of phosphorus pentachloride in 150 ml of dichloromethane were added in one portion 21.72 g (38 mm) of (Z)-2-(2-tert.-butoxycarbonylprop-2-oxyimino)-2-(2-triphenylmethylaminothiazol-4-yl)acetic acid. The reaction mixture was stirred for thirty minutes at −10° C., and then diluted with a cold solution of 100 ml of water containing 11.66 ml (83.6 mm) of triethylamine. The two-phase reaction mixture was stirred vigorously for about three minutes, and then the organic layer was removed and added to a stirred cold (−10° C.) suspension of 16.89 g (38.0 mm) of (6R,7R)-7-amino-3-(1-pyridiniummethyl)ceph-3-em-4-carboxylic acid dihydrochloride in 195 ml N,N-dimethylacetamide containing 26.5 ml (190 mm) of triethylamine. The reaction mixture was stirred at 0° to −5° C. for thirty minutes, and then was diluted by the addition in one portion of 300 ml of water. The aqueous reaction mixture was stirred for ten minutes, and then the organic layer was separated and further diluted by the addition of 150 ml of fresh N,N-dimethylacetamide and 300 ml of diethyl ether. The organic solution was stirred at 0° to 5° C. for one hour, and the crystalline precipitate that had formed was collected by filtration, washed with fresh N,N-dimethylacetamide and then with fresh diethyl ether, and was dried at ambient temperature in vacuum for sixteen hours to afford 20.96 g (65.2% yield) of (6R,7)-7-[(Z)-2-(2-triphenylmethylaminothiazol-4-yl)-2-(2-tert.-butoxycarbonylprop-2-oxyimino)acetamido]-3-(1-pyridiniummethyl)ceph-3-em-4-carboxylate N,N-dimethylacetamide solvate. Purity by high performance liquid chromatography was established at 95.56%.

EXAMPLE 2

The process of Example 1 was repeated as follows:

To a cold (−15° C.) stirred solution of 7.73 g (1.44 eq) of phosphorus pentachloride in 120 ml of dichloromethane were added in one portion 17.32 g (1.2 eq) of (Z)-2-(2-tert.-butoxycarbonylprop-2-oxyimino)-2-(2-triphenylmethylaminothiazol-4-yl)acetic acid. The reaction mixture was stirred for thirty minutes while maintaining the temperature at about −10° to −15° C. The reaction mixture was then diluted by the addition of 80 ml of water containing 10.5 ml (3.0 eq) of triethylamine. After stirring the reaction mixture for three minutes, the organic layer was separated and the aqueous layer was discarded. The organic layer was then added dropwise over ten minutes to a cold (−10° C.) stirred suspension of 11.13 g (1.0 eq) of (6R,7R)-7-amino-3-(1-pyridiniummethyl)ceph-3-em-4-carboxylic acid dihydrochloride in 88 ml of N,N-dimethylacetamide containing 17.5 ml (5.0 eq) of triethylamine. The reaction mixture was stirred for thirty minutes at about −5° to 0° C., and then was allowed to warm to about +5° C. and was diluted by the addition of 200 ml of water. After stirring the aqueous mixture for two minutes, the organic layer was separated and the aqueous layer was discarded. The organic layer was further diluted with 200 ml of ethyl acetate and 100 ml of diethyl ether, and the mixture was vigorously stirred at about 20° to 25° C. The mixture was seeded with ceftazidime intermediate N,N-dimethylacetamide solvate to initiate crystallization. After stirring the mixture for thirty minutes at 20° to 25° C., the temperature was lowered to 0° C. and stirring was continued for about two hours. Filtration of the mixture and washing of the filter cake with a mixture of 10 ml of N,N-dimethylacetamide and 10 ml of diethyl ether and finally with 40 ml of diethyl ether provided, following drying at 35° C. under vacuum for about sixteen hours, about 78 percent yield of ceftazidime intermediate N,N-dimethylacetamide solvate (1.5 mole of N,N-dimethylacetamide as demonstrated by NMR analysis).

EXAMPLE 3

The procedures of Examples 1 and 2 was repeated when 20.2 g (33.72 mM) of (Z)-2-(2-tert.-butoxycarbonylprop-2-oxyimino)-2-(2-triphenylmethylaminothiazol-4-yl)-acetic acid was reacted with 8.74 g (40.74 mM) of phosphorus pentachloride to produce the corresponding acid chloride, which was then reacted with 11.13 g (28.1 mM) of (6R,7R)-7-amino-3-(1-pyridiniummethyl)ceph-3-em-4-carboxylic acid dihydrochloride. Upon completion of the reaction, the mixture was washed with 400 ml of water. The organic layer was separated and further diluted by addition of 100 ml of ethyl acetate and 50 ml of diethyl ether. The reaction mixture was stirred while 50 ml of N,N-dimethylacetamide were added dropwise over fifteen minutes. The reaction mixture was stored at 25° C. for one hour and then cooled to 0° C. and stored at that temperature for ninety minutes. The crystalline precipitate was collected by filtration, washed with 20 ml of 50% (v/v) N,N-dimethylacetamide in diethyl ether, with 20 ml of diethyl ether and then was dried to provide 77.4% yield of crystalline ceftazidime intermediate DMAC solvate. The crystals were slurried in 280 ml of diethyl ether, filtered and dried to give crystalline mono-DMAC solvate. m.p. 151°–152° C. (dec).

NMR (CDCl$_3$): shows 1.02 equivalents of DMAC δ 1.36 (s, 9H); 1.53 (s, 6H); 2.08 (s, 3H); 2.93–3.00 (two s, 6H); 5.06 (d, 1H); 5.89 (m, 1H); 6.70 (s, 1H); 7.26 (s, 15H); 9.6, 8.2, 7.9 (pyridinium).

The following x-ray pattern was obtained on a sample of the above product:
114.6 mm Debye-Scherrer Camera
Copper target tube
Nickel filter

| d | I/I$_1$ |
| --- | --- |
| 16.07 | 1.00 |
| 10.53 | .12 |
| 9.72 | .12 |
| 9.07 | .72 |
| 8.23 | .04 |
| 7.66 | .24 |
| 7.17 | .04 |
| 6.84 | .04 |
| 6.30 | .24 |
| 6.01 | .16 |
| 5.77 | .16 |
| 5.42 | .24 |
| 5.25 | .16 |
| 4.82 | .20 b |
| 4.51 | .44 |
| 4.25 | .24 |
| 4.10 | .36 |
| 3.84 | .20 |
| 3.69 | .08 |
| 3.61 | .08 |
| 3.47 | .04 |
| 3.35 | .04 | b = broad

We claim:
1. In a process for preparing (6R,7R)-7-[(Z)-2-(2-triphenylmethylaminothiazol-4-yl)-2-(2-tert.-butoxycarbonylprop-2-oxyimino)acetamido]-3-(1-pyridiniummethyl)-ceph-3-em-4-carboxylate by reacting a (Z)-2-(2-tert.-butoxycarbonylprop-2-oxyimino)-2-(2-triphenylmethylaminothiazol-4-yl)-acetyl halide with (6R,7R)-7-amino-3-(1-pyridiniummethyl)ceph-3-em-4-carboxylic acid dihydrochloride, the improvement which comprises the steps of: (a) carrying out the reaction in N,N-dimethylacetamide and a water-immiscible organic solvent, (b) washing the reaction mixture with water, and (c) adding an organic counter-solvent selected from diethyl ether, methyl ethyl ether, diglyme, tetrahydrofuran, ethyl acetate or methyl acetate so as to produce a crystalline N,N-dimethylacetamide solvate.

2. The process of claim 1 wherein the acetyl halide employed is the acetyl chloride.

3. The process of claim 1 wherein the solvate produced contains about 1.0 mole of N,N-dimethylacetamide per mole of ceftazidime intermediate.

* * * * *